United States Patent
Couillard et al.

(10) Patent No.: US 7,322,925 B2
(45) Date of Patent: Jan. 29, 2008

(54) APPARATUS AND METHOD FOR MAKING PRE-FASTENED ABSORBENT UNDERGARMENTS

(75) Inventors: Jack L. Couillard, Menasha, WI (US); Robert Lee Popp, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 88 days.

(21) Appl. No.: 11/304,374

(22) Filed: Dec. 15, 2005

(65) Prior Publication Data

US 2007/0137011 A1 Jun. 21, 2007

(51) Int. Cl.
*B31F 1/00* (2006.01)

(52) U.S. Cl. .................. 493/450; 493/394; 493/416; 493/418

(58) Field of Classification Search ........... 493/393, 493/394, 416, 417, 418, 450; 156/202, 204, 156/227; 604/385.04, 389
See application file for complete search history.

(56) References Cited

U.S. PATENT DOCUMENTS

| | | | |
|---|---|---|---|
| 2,328,814 A | 9/1943 | Laukhuff | |
| 3,031,185 A | 4/1962 | Brien | |
| 3,196,874 A | 7/1965 | Hrubecky | |
| 3,552,736 A | 1/1971 | Frick et al. | |
| 3,604,015 A | 9/1971 | Dove | |
| 3,685,818 A | 8/1972 | Burger et al. | |
| 3,724,464 A | 4/1973 | Enloe | |
| 3,741,213 A | 6/1973 | Endres | |
| 3,774,610 A | 11/1973 | Eckert et al. | |
| 3,782,714 A | 1/1974 | Spencer et al. | |
| 3,848,595 A | 11/1974 | Endres | |
| 3,848,597 A | 11/1974 | Endres | |
| 3,905,592 A | 9/1975 | Spencer et al. | |
| 3,924,627 A | 12/1975 | Nystrand | |

(Continued)

FOREIGN PATENT DOCUMENTS

EP 0 217 032 A2 4/1987

(Continued)

OTHER PUBLICATIONS

International Search Report for PCT/US2006/015228, dated Aug. 23, 2006, 4 pages.

(Continued)

*Primary Examiner*—Louis Huynh
(74) *Attorney, Agent, or Firm*—Armstrong Teasdale, LLP

(57) ABSTRACT

In a method and apparatus for mechanically fastening a partially assembled absorbent undergarment during manufacture, a longitudinal folding device is carried by a transport device and moveable between an open configuration in which it receives a partially assembled undergarment, and a closed configuration in which the undergarment is folded longitudinally by the folding device. A first transverse folding device folds a first fastening portion of the undergarment relative to the folding device and generally toward a second fastening portion, and a second transverse folding device carried by the transport device folds the second fastening portion relative to the folding device and generally toward the first fastening portion to facilitate engagement therebetween. A separate retention member is carried by the transport device and draws at least one of the first and second fastening portions against the retention member while the garment is moved by the transport device.

9 Claims, 12 Drawing Sheets

U.S. PATENT DOCUMENTS

| | | |
|---|---|---|
| 3,968,799 A | 7/1976 | Schrading |
| 3,994,486 A | 11/1976 | Nystrand |
| 4,029,310 A | 6/1977 | Reist |
| 4,519,596 A | 5/1985 | Johnson et al. |
| 4,648,861 A | 3/1987 | Pierce |
| 4,663,220 A | 5/1987 | Wisneski et al. |
| 4,704,116 A | 11/1987 | Enloe |
| 4,822,328 A | 4/1989 | Bertolini et al. |
| 4,940,464 A | 7/1990 | Van Gompel et al. |
| 5,046,272 A | 9/1991 | Vogt et al. |
| 5,104,116 A | 4/1992 | Pohjola |
| 5,110,403 A | 5/1992 | Ehlert |
| 5,176,615 A | 1/1993 | Munsch |
| 5,224,405 A | 7/1993 | Pohjola |
| 5,226,992 A | 7/1993 | Morman |
| 5,486,166 A | 1/1996 | Bishop et al. |
| 5,490,846 A | 2/1996 | Ellis et al. |
| 5,766,389 A | 6/1998 | Brandon et al. |
| 5,779,831 A | 7/1998 | Schmitz |
| 5,820,973 A | 10/1998 | Dodge, II et al. |
| 6,395,115 B1 | 5/2002 | Popp et al. |
| 6,409,858 B1 | 6/2002 | Popp et al. |
| 6,432,243 B1 | 8/2002 | Popp et al. |
| 6,447,628 B1 | 9/2002 | Couillard et al. |
| 6,481,362 B2 | 11/2002 | Hietpas et al. |
| 6,497,032 B2 | 12/2002 | Maxton et al. |
| 6,513,221 B2 | 2/2003 | Vogt et al. |
| 6,514,187 B2 | 2/2003 | Coenen et al. |
| 6,562,167 B2 | 5/2003 | Coenen et al. |
| 6,565,691 B2 | 5/2003 | Tomsovic et al. |
| 6,596,113 B2 | 7/2003 | Csida et al. |
| 6,723,034 B2 | 4/2004 | Durrance et al. |
| 6,821,370 B2 | 11/2004 | Tomsovic et al. |
| 7,069,970 B2 | 7/2006 | Tomsovic et al. |
| 2003/0111168 A1 | 6/2003 | Olson et al. |
| 2003/0205312 A1 | 11/2003 | Tomsovic et al. |

FOREIGN PATENT DOCUMENTS

| | | |
|---|---|---|
| EP | 0 701 424 B1 | 3/1996 |
| EP | 1504738 A2 | 2/2005 |
| EP | 1552798 A1 | 7/2005 |
| JP | 7-205943 | 8/1995 |
| WO | WO 95/32639 A1 | 12/1995 |
| WO | WO 00/37009 A2 | 6/2000 |
| WO | WO 01/87206 A1 | 11/2001 |
| WO | WO 01/87216 A1 | 11/2001 |
| WO | WO 01/87217 A2 | 11/2001 |
| WO | WO 01/87218 A2 | 11/2001 |
| WO | WO 01/87753 A2 | 11/2001 |
| WO | WO 02/00152 A1 | 1/2002 |
| WO | WO 02/065961 A2 | 8/2002 |
| WO | WO 02/067835 A2 | 9/2002 |
| WO | WO 03/041624 A1 | 5/2003 |
| WO | WO 03/051247 A2 | 6/2003 |
| WO | WO 03/051248 A2 | 6/2003 |
| WO | WO 03/053321 A1 | 7/2003 |

OTHER PUBLICATIONS

International Search Report for PCT/US2006/030034 dated Jan. 30, 2007, 3 pages.

APPARATUS AND METHOD FOR MAKING PRE-FASTENED ABSORBENT UNDERGARMENTS

BACKGROUND

The present invention relates generally to apparatus and methods for making pre-assembled or pre-fastened absorbent undergarments, and more particularly to apparatus and methods for engaging cooperating fastening components of pre-fastened absorbent undergarments during the making of such undergarments.

Absorbent undergarments have numerous applications including, without limitation, diapers, training pants and adult incontinence products. A typical absorbent undergarment is formed as a composite structure including an absorbent assembly disposed between a liquid permeable bodyside liner and an outer cover. These components can be combined with other materials and features such as elastic materials and containment structures to form a product which is specifically suited to its intended purposes. A number of such undergarments include fastening components which are intended to be secured together (e.g., pre-fastened) during manufacture of the garment so that the product is packaged in it's fully assembled, ready-to-wear form.

As an example, a child's training pants conventionally has a central absorbent chassis and front and back side panels extending laterally out from the chassis adjacent longitudinally opposite ends thereof. Each of the front and back side panels has a fastening component thereon, such as a hook or a loop fastener. During manufacture of the training pants, the central absorbent chassis is initially formed generally flat and then folded over so that the front and back side panels face each other. The respective fastening components of the front and back side panels are then aligned and engaged with each other to pre-fasten the training pants in its fully assembled three-dimensional form.

However, existing techniques for making conventional absorbent undergarments such as the training pants described above or other pre-fastened undergarments in which fastening components are pre-fastened together during manufacture are in some respects inadequate. In particular, typical manufacturing processes are performed at high speeds, such as to make 250 or more pre-fastened absorbent undergarments per minute. One sometimes limiting factor is that folding of the undergarment while the garment is being moved along the machine direction at high speed requires reciprocating movement of a folding device in a direction orthogonal to the direction in which the undergarment web is moving. This can result in inconsistent locating of the fold line along which the garment is folded. Commonly used processes also require multiple stations along the manufacturing apparatus, such as one station at which the garment is folded and a separate station at which the side panels are subsequently fastened together. Specifically, multiple stations must be used so as to avoid any of the folding and engaging devices of the manufacturing line from becoming disposed within the interior of the pre-fastened garment, thereby inhibiting further movement of the garment along the line.

To this end, Japanese Laid-Open Patent Application No. 7-205943 discloses a folding device in which multiple pairs of suction folding means are provided on a rotating drum, with each pair of suction folding means being capable of both folding one absorbent garment and attaching the side edges of the garment together. In particular, as the drum rotates a respective pair of the suction folding means is in an open configuration in which the folding means are laid flat, or tangent relative to the rotating drum. In this configuration, a garment that has been cut from a web of such garments is suctioned flat onto the pair of suction folding means. Upon further rotation of the drum, adhesive is applied to the side edges of the garment. Further rotation of the drum causes the pair of suction folding means to fold inward toward each other while the garment is still suctioned to the respective folding means. The garment is thus folded in half to bring the ends of the garment together. The edges of the garment contact each other such that the adhesive holds the edges together in what is commonly referred to as a butt-seam. Finally, the drum is rotated to a position in which the suction folding means are opened again, whereby suction to one of the folding means is decreased so that the folded garment is held only by the other folding means and then transferred to a conveyor for further processing.

While such a folding device is intended to increase the processing speed for making folded garments, butt-seams are generally undesirable because they present an unfinished appearance. More desirable is what is commonly referred to as a lap seam in which the side edges of the garment at one end thereof overlap and are engaged with the side edges of the garment at the opposite end of the garment. For example, U.S. Pat. No. 5,779,831 discloses an apparatus that grips an unfolded undergarment in four locations and folds the undergarment in half. The gripped portions of the undergarment are then folded inward toward each other. As a result, portions of the undergarment adjacent to the gripped portions overlap each other and are bonded together by an ultrasonic bonding device. However, the portions of the undergarment that are to be bonded together are ungripped (i.e., the overlapping portions adjacent the gripped portions) and are therefore not positively held in opposed relationship. There is a risk that motion of the apparatus or other surrounding conditions can cause the portions that are to be bonded to become misaligned, folded or the like and result in a less than desireable bonding.

Also, while various other apparatus and processes for forming lap seams are known to those skilled in the art, such apparatus and processes typically require the lap seam forming to be conducted other than at the same station at which the folding of the garment occurs. As such, additional processing apparatus and time is needed to make such a lap seam.

SUMMARY

In accordance with one embodiment of apparatus for mechanically fastening an absorbent undergarment to reconfigure the undergarment from a partially assembled, unfastened configuration to a pre-fastened configuration during the initial manufacturing thereof, such apparatus generally comprises a transport device driven to move in a transport direction. A longitudinal folding device carried by the transport device in the transport direction is moveable relative to the transport device between an open configuration in which the longitudinal folding device receives an absorbent undergarment in its partially assembled configuration, and a closed configuration in which the absorbent undergarment is folded longitudinally by the folding device. A first transverse folding device carried by the transport device in the transport direction is operable to fold the first fastening portion of the undergarment relative to the folding device and generally toward the second fastening portion and a second transverse folding device carried by the transport device in the transport direction and operable to fold the second fastening portion of the undergarment relative to the folding device and generally toward the first fastening portion of the undergarment for generally opposed relationship between the first and second fastening portions to facilitate engagement therebetween. A retention member separate from the longitudinal folding device and the transverse folding device is carried by the transport device in the transport direction. The retention member is positioned relative to the longitudinal folding device and the transverse folding devices for interposition within the folding device in the closed configuration thereof. The retention member has a working surface and is operable to draw against said working surface at least one of the first fastening portion and the second fastening portion of the undergarment while the garment is moved by the transport device in the transport direction.

In one embodiment of a method for mechanically forming a pre-fastened absorbent undergarment during initial manufacture of the undergarment, an absorbent undergarment is partially assembled to have a configuration in which the undergarment is generally unfolded and the first and second fastening portions are unfastened. The absorbent undergarment is transported in a transport direction and folded longitudinally such that first and second end regions of the undergarment are in generally opposed relationship with each other. The longitudinal folding step is performed while transporting the partially assembled garment in the transport direction. A first fastening portion of the undergarment is urged to fold in toward the second fastening portion and toward the working surface of a retention member, with this first urging step being performed while transporting the undergarment and the retention member in the transport direction. The retention member is operated to draw against and retain thereon the first fastening portion, with this step being performed while transporting the undergarment and the retention member in the transport direction. A second fastening portion of the undergarment is urged to fold in toward the first fastening portion retained on the working surface of the retention member for overlapping relationship between the first and second fastening portions to thereby facilitate fastening engagement therebetween while retaining the first fastening portion on the working surface of the retention member. This second urging step is performed while transporting the undergarment and the retention member in the transport direction.

In another embodiment of a method for mechanically forming a pre-fastened absorbent undergarment during initial manufacture of the undergarment, an absorbent undergarment is partially assembled to have a configuration in which the undergarment is generally unfolded and first and second fastening portions of the undergarment are unfastened. The undergarment is transported in a transport direction. The absorbent undergarment is folded longitudinally such that first and second end regions of the undergarment are in generally opposed relationship with each other, with this longitudinal folding step being performed while transporting the partially assembled garment in the transport direction. A first fastening portion of the undergarment is folded in toward a second fastening portion while transporting the undergarment in the transport direction. Substantially the entire second fastening portion is retained on a transverse folding device while moving the transverse folding device relative to the first fastening portion to a position in which the transverse folding device is in generally opposed relationship with the first fastening portion with the second fastening portion retained on the transverse folding device and disposed between the transverse folding device and the first fastening portion such that the second fastening portion fastenably engages the first fastening portion.

BRIEF DESCRIPTION OF THE DRAWINGS

Corresponding reference characters indicate corresponding parts throughout the drawings.

DETAILED DESCRIPTION

The methods and apparatus of the present invention may be used to make a variety of absorbent undergarments including, without limitation, diapers, training pants, feminine hygiene products, incontinence products, medical garments, other personal care or health care garments, swim pants, athletic clothing, pants and shorts, and the like. For ease of explanation, the methods and apparatus of the present invention are hereafter particularly described in connection with making pre-fastened child's training pants, generally indicated as 20 in FIG. 1. In particular, the methods and apparatus will be described in terms of those for making pre-fastened disposable training pants similar to the pants described in published PCT Application No. WO 00/37009, published Jun. 29, 2000 by A. L. Fletcher et al., the disclosure of which is incorporated herein by reference. The training pants 20 may also be constructed using the methods and apparatus disclosed in U.S. Pat. No. 4,940,464 issued Jul. 10, 1990 to VanGompel et al.; and U.S. Pat. No. 5,766,389 issued Jun. 16, 1998 to Brandon et al.; the disclosures of which are also incorporated herein by reference.

Figure 1:
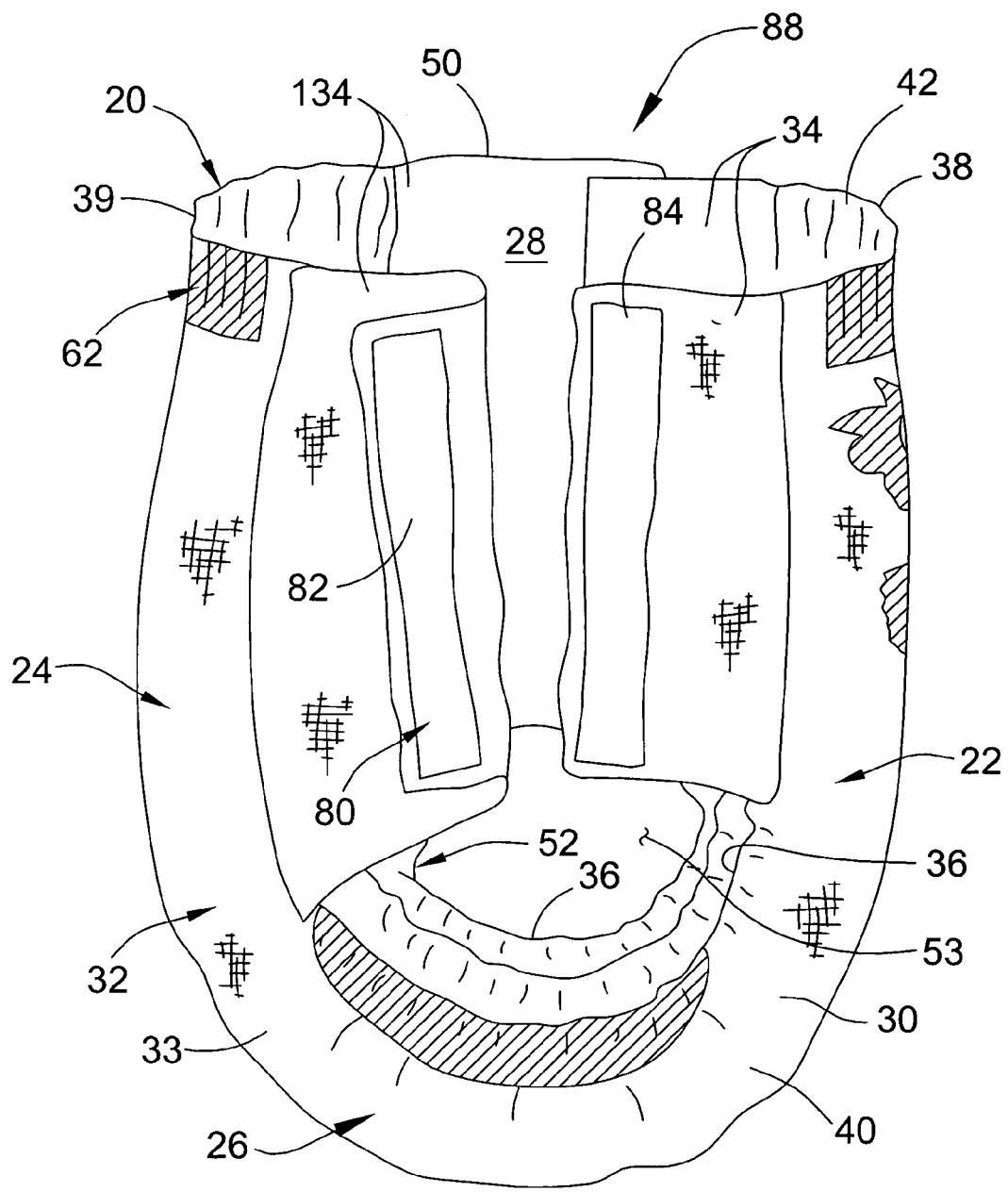
FIG. 1 is a side elevation of on embodiment of an absorbent undergarment in the form of a child's training pants with a fastening system of the training pants shown fastened on one side of the training pants and unfastened on the opposite side of the training pants.

With reference now to the drawings, and in particular to FIG. 1, the training pants 20 are illustrated in a partially fastened condition and comprise an absorbent chassis 32 and a fastening system 80. The absorbent chassis 32 has a front waist region 22 (broadly, a first longitudinal end region), a back waist region 24 (broadly, a second longitudinal end region), and a crotch region 26 (broadly, a central region) extending between and interconnecting the front and back waist regions, an inner surface 28 which faces the wearer, and an outer surface 30 which is opposite the inner surface and faces away from the wearer. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
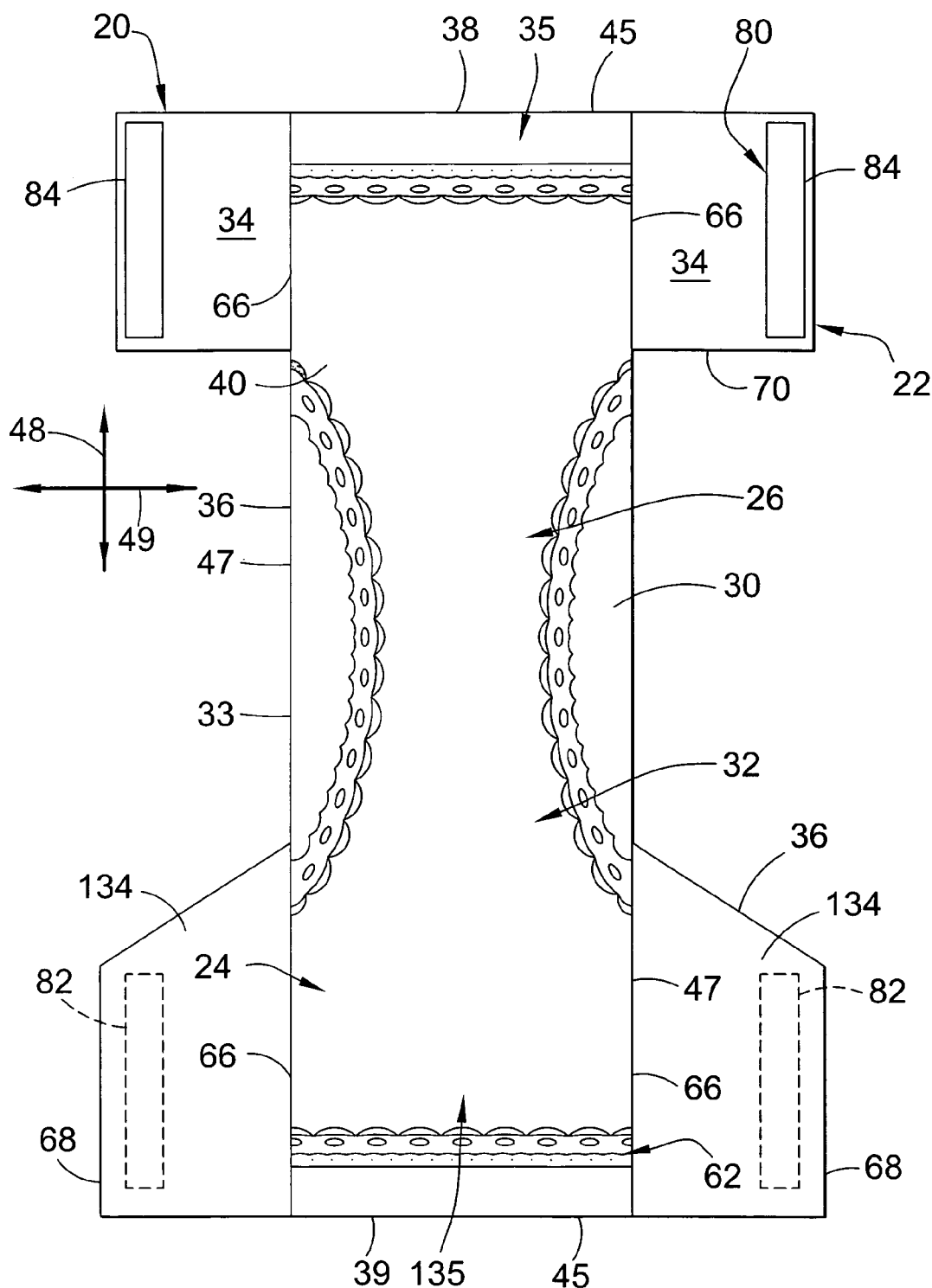
FIG. 2 is a bottom plan view of the training pants of FIG. 1 in an unfastened, unfolded and laid flat condition to show the surface of the training pants which faces away from the wearer.
Figure 3:
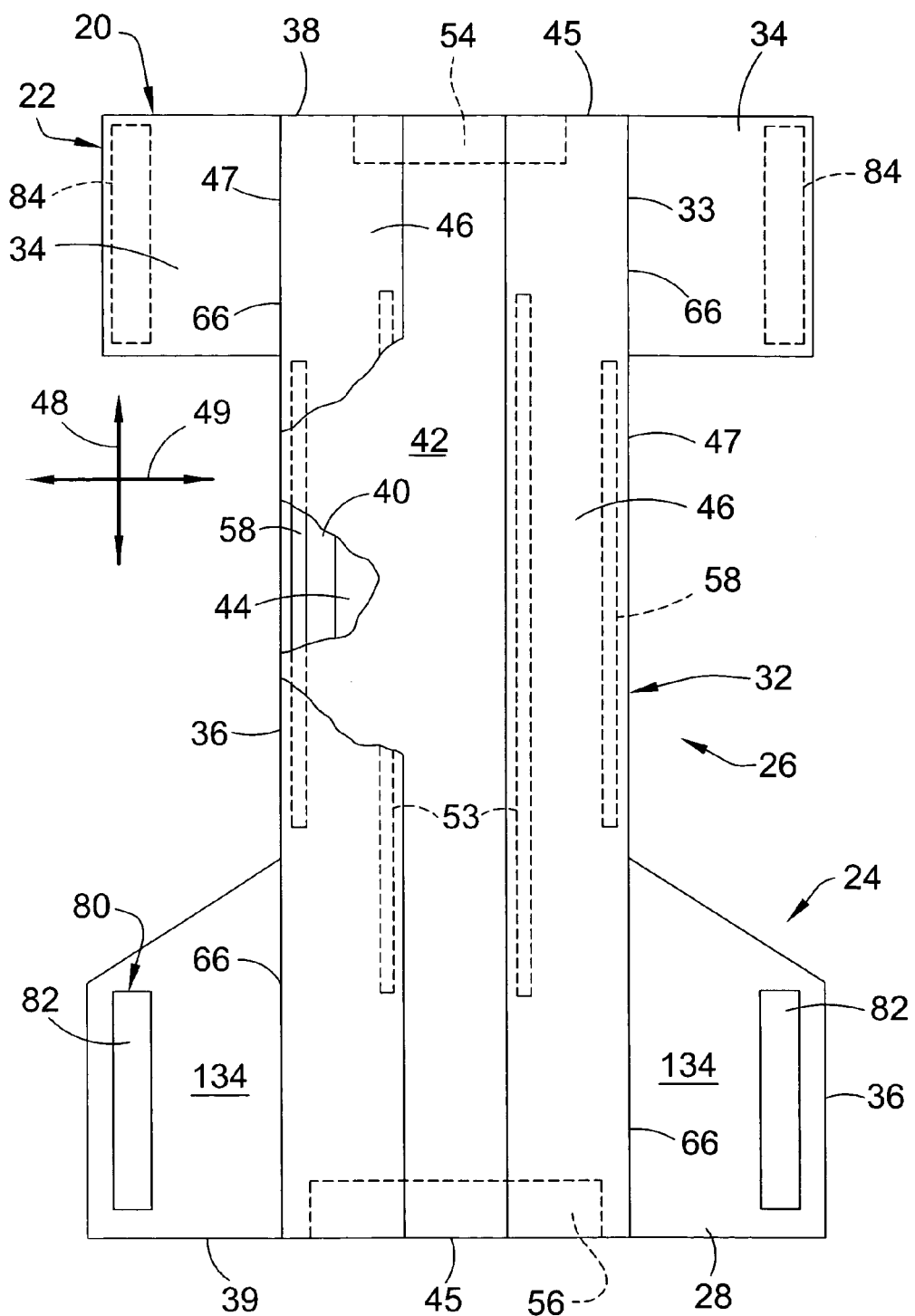
FIG. 3 is a top plan view of the training pants it its unfastened, unfolded and laid flat condition to show the surface of the training pants which faces the wearer, with portions of the training pants being cut away to reveal underlying features.

The illustrated absorbent chassis 32 comprises a composite structure 33 which when laid flat can be rectangular or any other desired shape, and has a pair of laterally opposite front side panels 34 and a pair of laterally opposite back side panels 134 extending outward therefrom. The composite structure 33 and side panels 34 and 134 may comprise two or more separate elements, as shown in FIG. 1, or be integrally formed. Integrally formed side panels 34, 134 and composite structure 33 would comprise at least some common materials, such as the bodyside liner, flap composite, outer cover, other materials and/or combinations thereof, and/or could define a one-piece elastic, stretchable, or non-stretchable pants. The illustrated composite structure 33 comprises an outer cover 40, a bodyside liner 42 (FIGS. 1 and 3) which is connected to the outer cover in a superposed relation, an absorbent assembly 44 (FIG. 3) which is located between the outer cover and the bodyside liner, and a pair of containment flaps 46 (FIG. 3). The illustrated composite structure 33 has opposite ends 45 which form portions of the front and back waist edges 38 and 39, and opposite side edges 47 which form portions of the side edges 36 of the absorbent chassis 32 (FIGS. 2 and 3). For reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are secured together to define a three-dimensional pants configuration having a waist opening 50, a pair of leg openings 52 and an interior space 53. The front waist region 22 comprises the portion of the training pants 20 which, when worn, is positioned on the front of the wearer while the back waist region 24 comprises the portion of the training pants which, when worn, is positioned on the back of the wearer. The crotch region 26 of the training pants 20 comprises the portion of the training pants 20 which, when worn, is positioned between the legs of the wearer and covers the lower torso of the wearer. The front and back side panels 34 and 134 comprise the portions of the training pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily has a pair of containment flaps 46 (FIG. 3) which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the training pants 20 to form a seal against the wearer's body. The containment flaps 46 can be located along the side edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 desirably although not necessarily include a front waist elastic member 54, a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the composite structure 33.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate.

The outer cover 40 suitably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and desirably one that provides a generally cloth-like texture. The inner layer of the outer cover 40 can be both liquid and vapor impermeable, or can be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. Alternatively, the bodyside liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent assembly 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The outer cover 40, bodyside liner 42 and other materials used to construct the pants may comprise elastomeric or nonelastomeric materials.

The absorbent assembly 44 (FIG. 3) is positioned between the outer cover 40 and the bodyside liner 42, which can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Typically, a superabsorbent material is capable of absorbing at least about 15 times its weight in water, and desirably is capable of absorbing more than about 25 times its weight in water. As a general rule, the superabsorbent material is present in the absorbent assembly 44 in an amount of from 0 to about 90 percent weight based on total weight of the absorbent assembly. The absorbent assembly 44 may or may not be wrapped or encompassed by a suitable tissue wrap that may help maintain the integrity and/or shape of the absorbent assembly.

The absorbent chassis 32 can also incorporate other materials designed primarily to receive, temporarily store, and/or transport liquid along the mutually facing surface with absorbent assembly 44, thereby maximizing the absorbent capacity of the absorbent assembly. One suitable material is referred to as a surge layer (not shown) and may be located adjacent the absorbent structure 44 (e.g., between the absorbent structure and the liner 42) and attached to various components of the article 20 such as the absorbent structure and/or the bodyside liner 42 by methods known in the art, such as by adhesive, ultrasonic or thermal bonding. A surge management layer helps to decelerate and diffuse surges or gushes of liquid that may be rapidly introduced into the absorbent structure 44. Desirably, the surge management layer can rapidly accept and temporarily hold the liquid prior to releasing the liquid into the storage or retention portions of the absorbent structure 44. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are incorporated by reference herein.

As noted previously, the front and back side panels 34 and 134 are disposed on laterally opposite sides of the absorbent chassis 32 in longitudinally spaced relationship with each other. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 may be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can comprise a generally wider portion of the outer cover 40, the bodyside liner 42, and/or another component of the absorbent chassis 32. The front and back side panels 34 and 134 can be permanently bonded together or be releasably engaged with one another as illustrated by the fastening system 80.

The side panels 34, 134 may, but need not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The illustrated training pants 20 includes the fastening system 80 for refastenably securing the training pants about the waist of the wearer. The illustrated fastening system 80 includes first fastening components 84 adapted for refastenable engagement to corresponding second fastening components 82. In one embodiment, one surface of each of the first fastening components 84 comprises a plurality of engaging elements which project from that surface. The engaging elements of the first fastening components 84 are adapted to repeatedly engage and disengage engaging elements of the second fastening components 82.

The fastening components 84, 82 can comprise separate elements bonded to the side panels 34, 134, or they may be integrally formed with the side panels. Thus, unless otherwise specified, the term "fastening component" includes separate components which function as fasteners, and regions of materials such as side panels which function as fasteners. Moreover, a single material can define multiple fastening components to the extent that different regions of the material function as separate fasteners. The fastening components 84, 82 can be located on the side panels 34, 134, between the side panels such as on the absorbent chassis, or a combination of the two. The fastening components 84, 82 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 84 comprise hook fasteners and the second fastening components 82 comprise complementary loop fasteners. In another particular embodiment, the first fastening components 84 comprise loop fasteners and the second fastening components 82 comprise complementary hook fasteners. Alternatively, the fastening components 84, 82 may comprise interlocking similar surface fasteners, adhesive or cohesive fastening elements such as an adhesive fastener and an adhesive-receptive landing zone or material; or the like. Although the training pants 20 illustrated in FIG. 1 show the back side panels 134 overlapping the front side panels 34, the training pants 20 may instead be configured so that the front side panels overlap the back side panels.

With particular reference to FIG. 3, the fastening components 82 are disposed on the inner surface 28 of the back side panels 134. The fastening components 82 are suitably positioned along the laterally outer edges of the back side panels 134 and broadly define laterally spaced second fastening portions at the back or second end region 24 of the pants 20. With particular reference to FIG. 2, the second fastening components 84 are disposed on the outer surface 30 of the front side panels 34. The second fastening components 84 are sized to receive the first fastening components 82 and are suitably positioned along the outer edges of the front side panels 34 to broadly define laterally spaced first fastening portions at the front or first end region 22 of the pants 20. It is understood that the fastening components 82, 84 may also extend laterally out beyond the outer edges of the side panels 134, 34. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the outwardly-directed hooks. As used herein, the term fastening portion is intended to broadly refer to those portions of the garment that are to be overlapped with and fastenably engaged with each other to form the pre-fastened (e.g., three dimension ready-to-wear) configuration of the pants 20.

The fastening components 84, 82 can be adhered to the respective side panels 34, 134 by any means known to those skilled in the art such as adhesive bonds, ultrasonic bonds or thermal bonds. The fastening components 84, 82 may comprise separate fastening elements or distinct regions of an integral material. For example, the training pants 20 can include an integral second fastening material disposed in the front waist region 22 for refastenably connecting to the first fastening components 82 at two or more different regions, which define the second fastening components 84 (FIG. 1). In a particular embodiment, the fastening components 82, 84 can comprise integral portions of the waist regions 24, 22. For instance, one of the elastomeric front or back side panels 34, 134 can function as second fastening components 84 in that they can comprise a material which is releasably engageable with fastening components 82 disposed in the opposite waist region.

When engaged, the illustrated fastening components 82, 84 (and more suitably the first and second fastening portions) of the pants 20 define refastenable engagement seams 88 (FIG. 1). For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between a set of fastening components 82, 84 is measured parallel to the transverse axis 49 between the longitudinal center lines of the fastening component, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may only be partially laterally opposite each other, such as by being offset longitudinally, without departing from the scope of this invention.

Figure 4:
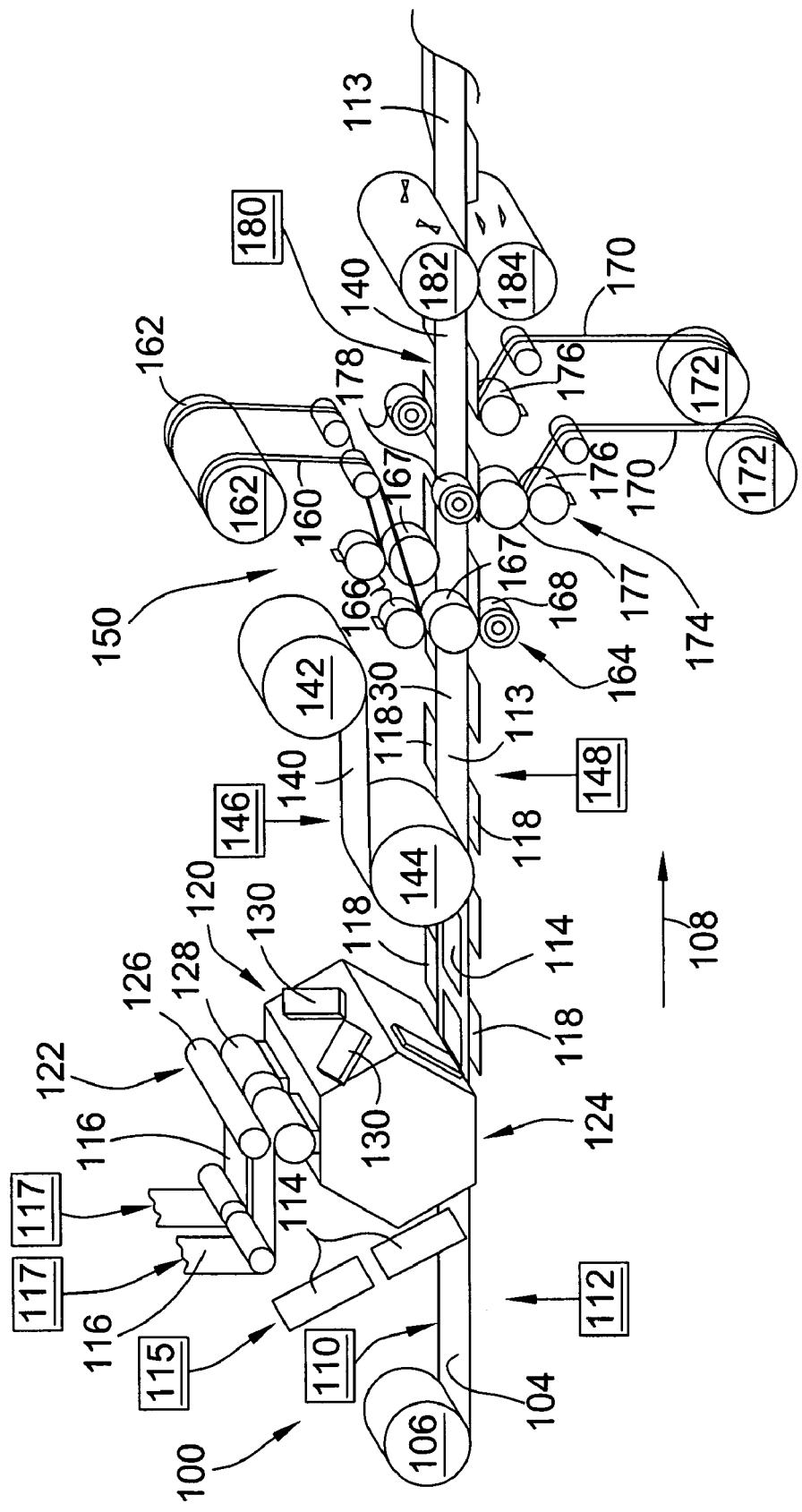
FIG. 4 is a schematic of an assembly system for making absorbent undergarments such as the training pants of FIGS. 1-3.

FIG. 4 generally illustrates one embodiment of a suitable assembly system, generally indicated at 100, for assembling a continuous web of absorbent undergarments to be subsequently cut into discrete undergarments such as the training pants 20 of FIGS. 1-3 and then pre-fastened together in their fully assembled or pre-fastened configuration. The various components of the training pants 20 can be secured together in the assembly system 100 by any means known to those skilled in the art such as, for example, adhesive, thermal and/or ultrasonic bonds. Certain garment manufacturing equipment which is readily known and understood in the art, including frames and mounting structures, ultrasonic and adhesive bonding devices, transport conveyors, transfer rolls, guide rolls, tension rolls, and the like, are well know in the art and have not been illustrated in FIG. 4. As an example, suitable absorbent supply mechanisms, web unwinds, conveyor systems, registration systems, drive systems, control systems and the like are disclosed in U.S. Pat. No. 5,766,389 issued Jun. 16, 1998 to Brandon et al., the entire disclosure of which is incorporated herein by reference.

With particular reference to the assembly system 100 illustrated in FIG. 4, a continuous supply of material 104 used to form the bodyside liner 42 is provided from a supply source 106. The supply source 106 can comprise for example any standard unwind mechanism, which generally includes a pair of spindles, a festoon assembly, and a dancer roll for providing bodyside liner material 104 at a desired speed and tension. Various components can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream from the supply source 106 for attaching pre-assembled containment flaps to the bodyside liner material 104. As various components are added in the assembly system 100, a continuously moving product assemblage 113 is formed.

A plurality of absorbent assemblies 114 can be provided from a suitable supply source 115. The supply source 115 can be any conventional mechanism for supplying the absorbent assemblies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent assemblies 114 can be disposed intermittently on the continuously moving bodyside liner material 104, one for each pair of training pants. The position of the absorbent assemblies 114 can be registered with the position of the surge material, if employed. The absorbent assemblies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34, 134 can be provided from suitable supply sources 117. The supply sources 117 can comprise one or more standard unwind mechanisms. The side panel material 116 can be cut into individual strips 118 and positioned partially on the bodyside liner material 104 using an applicator device 120. In the cross machine direction, the individual strips 118 desirably extend laterally outward from the bodyside liner material 104 (see FIGS. 4 and 7) and overlap the bodyside liner material by an amount such as about 2 or more centimeters to permit bonding of the strips to the bodyside liner and/or the containment flap material. In the machine direction 108, the position of the strips 118 can be registered relative to the absorbent assemblies 114 so that the product assemblage 113 can be cut between the absorbent assemblies with each strip 118 of side panel material 116 forming both a front side panel 34 and a back side panel 134 of consecutive pants.

One suitable applicator device 120 is disclosed in U.S. Pat. No. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 can continue to rotate toward the cutting assembly 122 to receive other strips. As disclosed by Van Gompel et al., the material 116 used to form the side panels can alternatively be provided in continuous form and pressurized fluid-jets or a rotary die cutter can be employed to cut the material to form leg openings 52 of the undergarment. Still alternatively, the side panels 34, 134 of the training pants 20 can be provided by portions of the bodyside liner 42, outer cover 40 and/or other components of the pants.

A continuous supply of material 140 used to form the outer cover 40 can be provided from a supply roll 142 or other suitable source. The outer cover material 140 can be transported over a laminator roll 144 and banded to the bodyside liner material 104. The absorbent assemblies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104 and 140. Alternatively, leg elastics or waist elastics can be initially bonded to the bodyside liner material 104 or another material.

Bonding devices 148 such as ultrasonic bonders can be employed downstream from the laminator roll 144 to bond the bodyside liner material 104, side panel material 116 and outer cover material 140. For example, these materials can be transported between a rotary ultrasonic horn and an anvil roll. Suitable rotary ultrasonic horns are described in U.S. Pat. No. 5,110,403 to Ehlert, which is incorporated herein by reference. The bonding devices 148 could otherwise be a thermal, pressure or adhesive bonding device as are well known.

The continuously moving product assemblage 113 next advances to a fastener application station 150 where fastening components 82, 84 are bonded to the strips 118 of side panel material 116. The location of the fastening components on the composite is a function in part of the configuration of the assembly system 100. As illustrated in FIG. 4, the assembly system 100 is configured so that the upward facing surface of the product assemblage 113 will become the outer surface 30 of the training pants 20 and the downward facing surface will become the inner surface 28. Moreover, the illustrated assembly system 100 is configured to produce partially assembled training pants having the front waist region 22 of a leading garment connected to the back waist region 24 of a trailing garment. However, it is understood that the assembly system 100 could alternatively employ any combination of different orientations. For example, the upward facing surface of the product assemblage 113 could form the inner surface 28 of finished garments. Additionally or alternatively, the back waist region 24 of a leading garment can be connected to the front waist region 22 of the trailing garment, or the garments can be arranged in a front-to-front/back-to-back relationship. Still alternatively, the assembly system 100 could be constructed as a cross-machine direction process wherein the longitudinal axis 48 of each garment could be perpendicular to the machine direction 108 during part or all of the assembly process.

Figure 5:
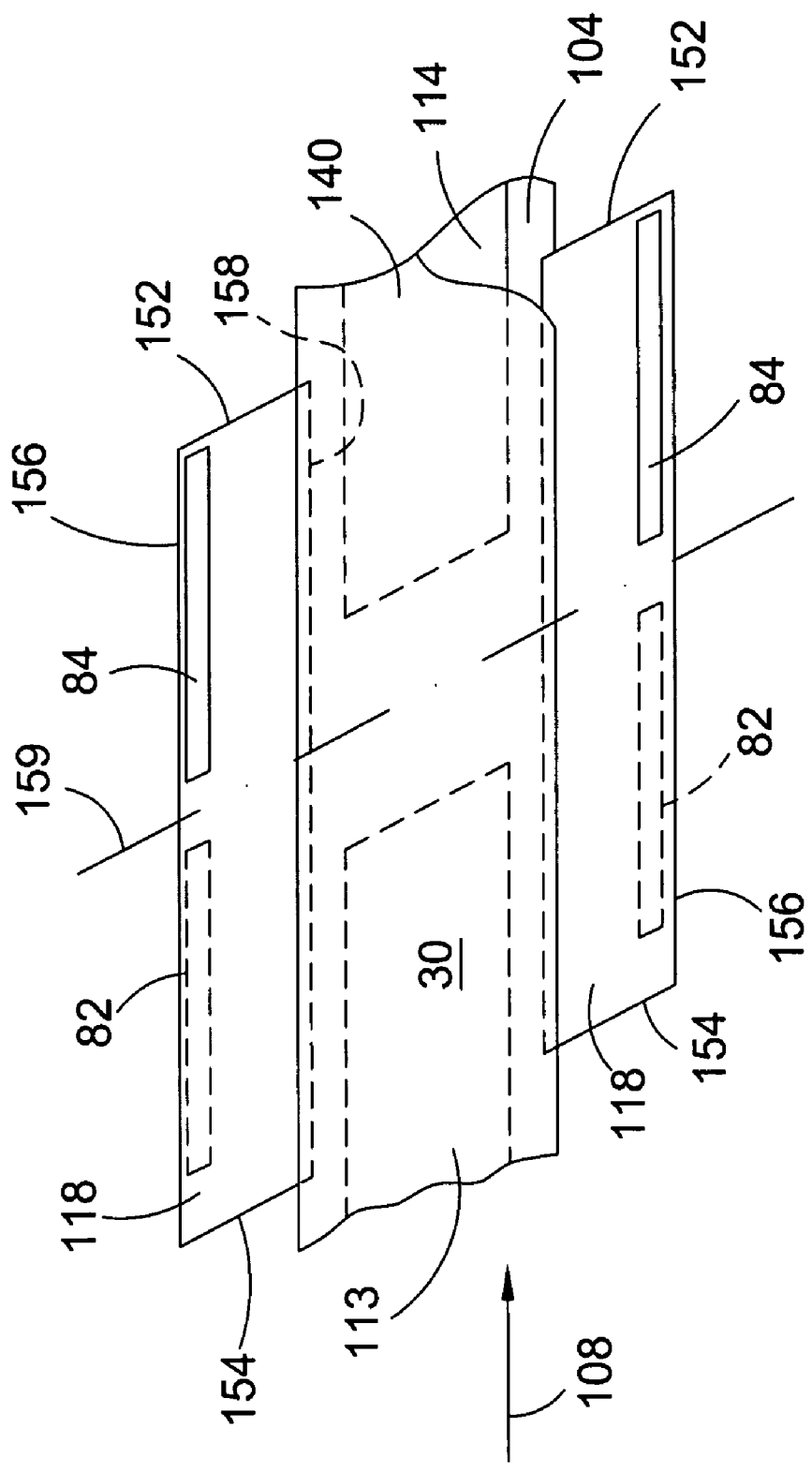
FIG. 5 is a schematic of a portion of a continuously moving assemblage or web of undergarments at one location along the assembly system of FIG. 4.

The locations of the fastening components 82, 84 in this embodiment are best illustrated in FIG. 5, which shows a portion of the product assemblage 113 moving in the direction of arrow 108 immediately following the fastener application station 150. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide discrete partially assembled training pants. Based on the illustrated orientation of the continuously moving product assemblage 113, the first fastening components 82 can be bonded to the underside of the strips 118 and the second fastening components 84 can be bonded to the top of the strips. Additionally, the first fastening components 82 can be disposed relatively closer to the trailing edge 154 and the second fastening components 84 can be disposed relatively closer to the leading edge 152. The first fastening components 82 can be spaced in the machine direction 108 from the second fastening components 84 so that the cut line 159 passes therebetween.

With reference again to FIG. 4, continuous webs of a second fastener material 160 used to form the second fastening components 84 can be provided from supply rolls 162 or other suitable sources. The second fastener materials 160 can be cut into individual second fasteners 84 by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and adhered on the top surfaces of the strips 118 of side panel material 116. Similarly, continuous webs of first fastener material 170 used to form the first fastening components 82 can be provided from supply rolls 172 or other suitable sources. The first fastener materials 170 can be cut into individual first fastening components by cutting assemblies 174 or other suitable devices. The illustrated cutting assemblies 174 include rotatable knife rolls 176, rotatable vacuum anvil rolls 177, and rotatable backing rolls 178. The continuous first fastener materials 170 can be cut by blades on the knife rolls 176, maintained on the anvil rolls 177 by vacuum, and adhered on the undersides of the strips 118 of side panel material 116.

It is contemplated that other arrangements can be used to attach the fastening components 82, 84 to the side panel material 116. For example, the fastening components 82, 84 can be applied to the side panel material 116 prior to uniting the side panel material with the bodyside liner material 104 and/or the outer cover material 140; the fastening components can be applied to the bodyside liner material 104 and/or outer cover material 140, whether separate side panels 34, 134 are used or not; portions of other components such as the bodyside liner and/or outer cover can form one or more of the fastening components; the separate side panels or integral side panels can themselves form one or more of the fastening components; the fastening components 82, 84 can be attached as pre-engaged composites or the like without departing from the scope of this invention.

After the fastening components 82, 84 are disposed on the strips 118 of side panel material 116, bonding devices 180 such as ultrasonic bonders, thermal bonders, pressure bonders, adhesive bonders or other suitable bonding devices can be employed to bond the fastening components to the strips. For example, the strips 118 can be transported between a rotary ultrasonic horn and an anvil roll, which devices are positioned on each side of the process at the cross machine direction location of the fastening components 82, 84. The strips 118 of side panel material 116 can be trimmed, for example, to provide angled and/or curved portions of the side panel material in the back waist region 24 (FIGS. 2 and 3). To this end, the assembly system 100 can include a die cutting roll 182 and a backing roll 184. In the illustrated embodiment, a portion of each strip 118 is trimmed from the trailing edge 154 (FIG. 7) in order to form the angled and/or curved portions in the back waist region 24.

Figure 6:
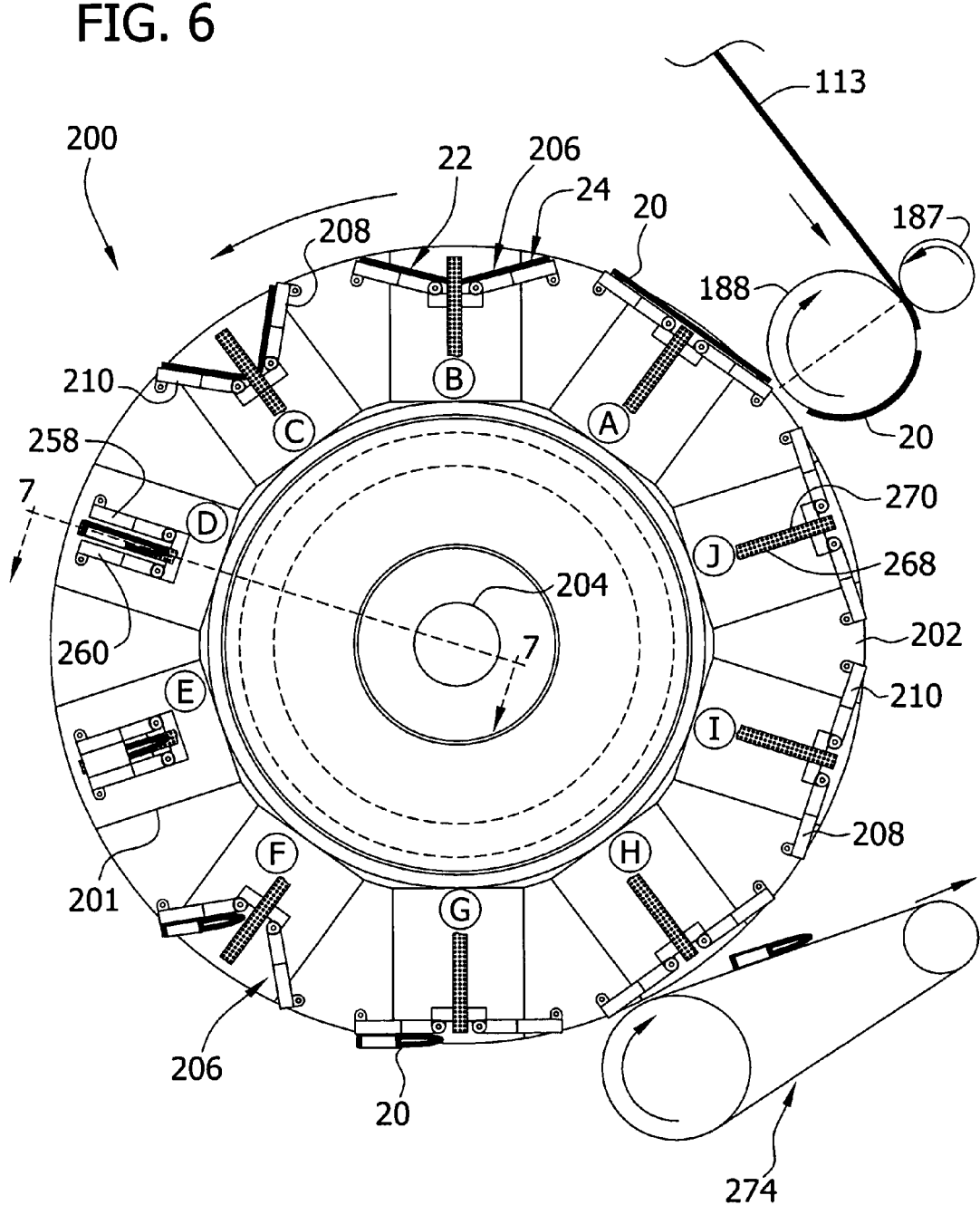
FIG. 6 is a schematic side elevation of one embodiment of fastening apparatus for folding and pre-fastening absorbent undergarments during the initial manufacture thereof.

With particular reference now to FIG. 6, the continuous assemblage 113 of partially assembled training pants is fed through a nip formed between a cutting roll 187 and an anvil roll 188 to cut the web into discrete, partially assembled training pants 20 (broadly, undergarments). The cutting roll 187 can include one or more flexible hardened steel blades whereby the pinching force between the blade on the cutting roll 187 and the anvil roll 188 creates the cut. The cutting roll 187 can have one or more blades depending upon the desired distance between the cuts. The anvil roll 188 of the illustrated embodiment is suitably a vacuum anvil roll so that the discrete, partially assembled training pants are held by suction on the outer surface of the anvil roll after cutting.

FIG. 6 particularly illustrates one embodiment of apparatus, generally indicated at 200, for reconfiguring partially assembled absorbent undergarments to a folded and pre-fastened configuration in which the undergarments are fully assembled and ready to wear, such as the training pants 20 of FIG. 1. The vacuum anvil roll 188 is suitably located adjacent the fastening apparatus 200 for transferring the discrete, partially assembled training pants immediately to the apparatus in an unfastened and unfolded condition following cutting. It is understood, however, that the anvil roll 188 need not be a vacuum anvil roll and may be located distally from the fastening apparatus 200, with the discrete training pants 20 being delivered to the fastening apparatus by conveyor or other suitable transfer devices without departing from the scope of this invention. Broadly, then, the fastening apparatus 200 receives discrete, partially assembled absorbent undergarments (e.g., assembled but otherwise with the fastening components unfastened to each other and the garment unfolded) from a source of partially assembled absorbent garments. The source of partially assembled absorbent undergarments may comprise the assembly system 100 and cutting and anvil rolls 187, 188 described previously and illustrated in FIGS. 4 and 6, or another suitable assembly system and transfer device.

Moreover, in the illustrated embodiment the discrete training pants 20 are delivered in their longitudinal direction (e.g., parallel to longitudinal axis 48) to the fastening apparatus 200, and in particular front end 38 first with the outer cover 40 facing down against the fastening apparatus. However, it is understood that the discrete undergarments 20 may be delivered longitudinally to the fastening apparatus 200 back end 39 first, or they may be delivered transversely (e.g., side edge 36 first) to the fastening apparatus, of they may be delivered to the fastening apparatus 200 in a generally stacked arrangement and the entire undergarment overlayed onto the fastening apparatus at once without departing from the scope of this invention.

The fastening apparatus 200 of the illustrated embodiment comprises a drum (broadly, a transport device), 202 on which one or more of the discrete, partially assembled training pants 20 are carried during pre-fastening of the pants. The drum 202 is constructed of suitable frame structure 201 (FIG. 6) and is operatively connected to a central shaft 204 that is in turn driven by a suitable drive motor (not shown) for rotation on the axis of the shaft to define a transport direction in which the drum (broadly, the transport device) moves as indicated by the direction arrow in FIG. 6. A plurality of longitudinal folding devices, generally indicated at 206, are carried by the drum 202 (e.g., ten such longitudinal folding devices are illustrated on the drum of FIG. 6) in the transport direction. The number of folding devices 206 may vary depending at least in part on the size of the drum, the size of the undergarment to be pre-fastened, and the desired speed of the manufacturing line of which the fastening apparatus 200 is part. As will be further discussed in detail herein, each folding device 206 is configured to receive the partially assembled training pants 20 and hold the training pants on the longitudinal folding device so that the drum, the longitudinal folding device and the training pants together move in the transport direction. The longitudinal folding device 206 is also operable to fold the training pants 20, e.g., with the front and back waist regions 22, 24 of the training pants in opposed relationship with each other, as the folding device is moved in the transport direction.

Each longitudinal folding device 206 of the illustrated embodiment suitably comprises a pair of folding plates 208, 210 that are moveable relative to the drum 202 (i.e., the transport device) between an open configuration (e.g., as illustrated at angular positions A, G, H, I and J in FIG. 6) in which the plates lie generally in the same plane as each other and are oriented generally tangentially relative to the drum and a closed configuration (e.g., as illustrated at angular positions D and E in FIG. 6) in which the plates are in opposed relationship with each other and oriented generally radially relative to the drum. The term longitudinal as used herein in reference to the folding device 206, and more particularly to the folding plates 208, 210, refers to the direction extending from one end of each folding plate to the opposite end of the same folding plate. For example, in the open configuration of the longitudinal folding device 206 the longitudinal direction of each folding plate 208, 210 is tangential to the drum 202 and in the closed position of the folding device the longitudinal direction of each folding plate is generally parallel to the radius of the drum. The terms transverse and lateral as used herein in reference to the folding device 206 refer to the direction orthogonal to both the longitudinal direction and the radius of the drum 202, such as parallel to the rotation axis of the drum. The folding plates 208, 210 are suitably disposed adjacent the circumference of the drum 202 in the open configuration of the plates, and are drawn relatively inward of the drum circumference in the closed configuration of the folding device 206.

Figure 7:
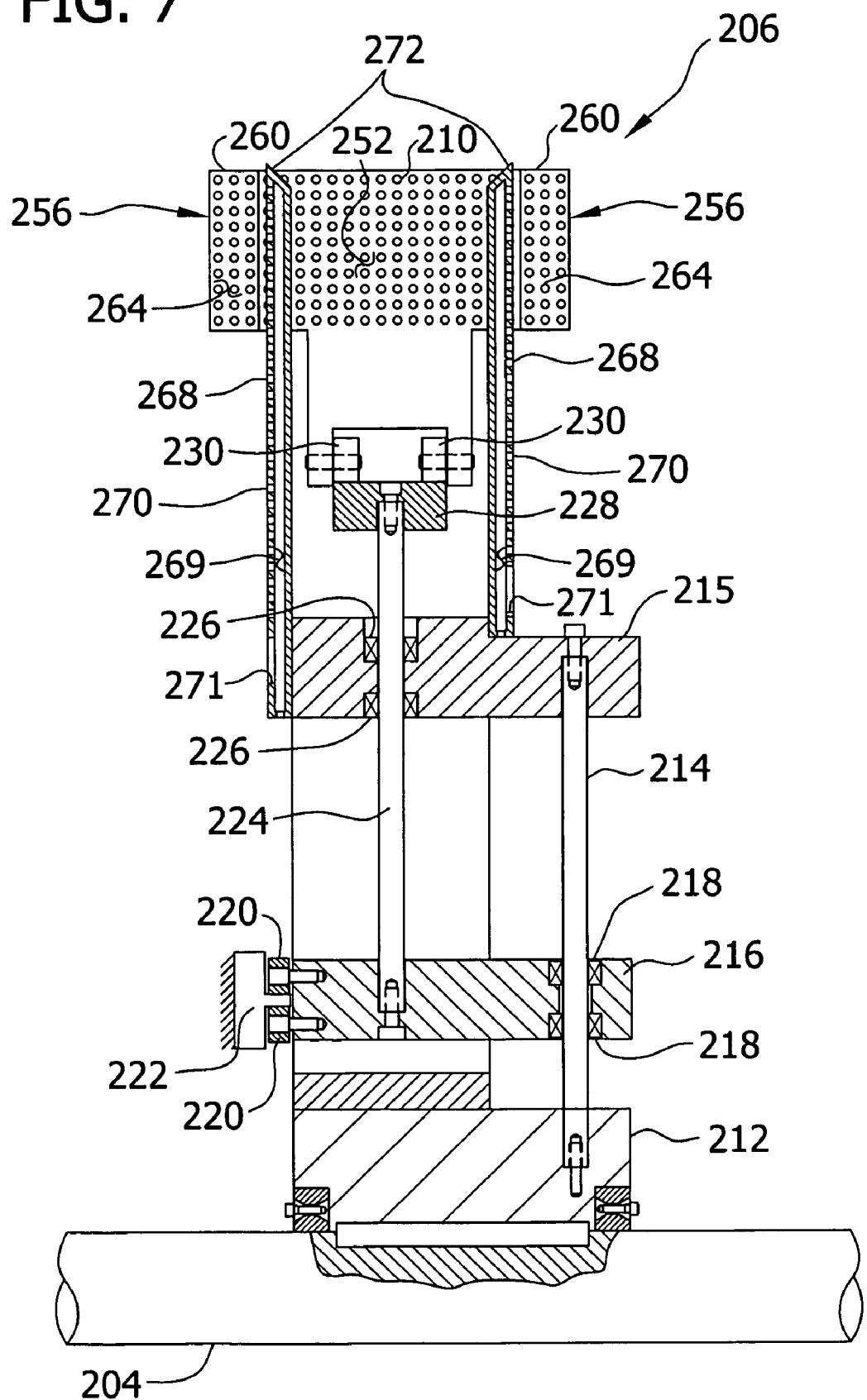
FIG. 7 is section taken in the plane of line 7-7 of FIG. 7, with the absorbent undergarment omitted.
Figure 8:
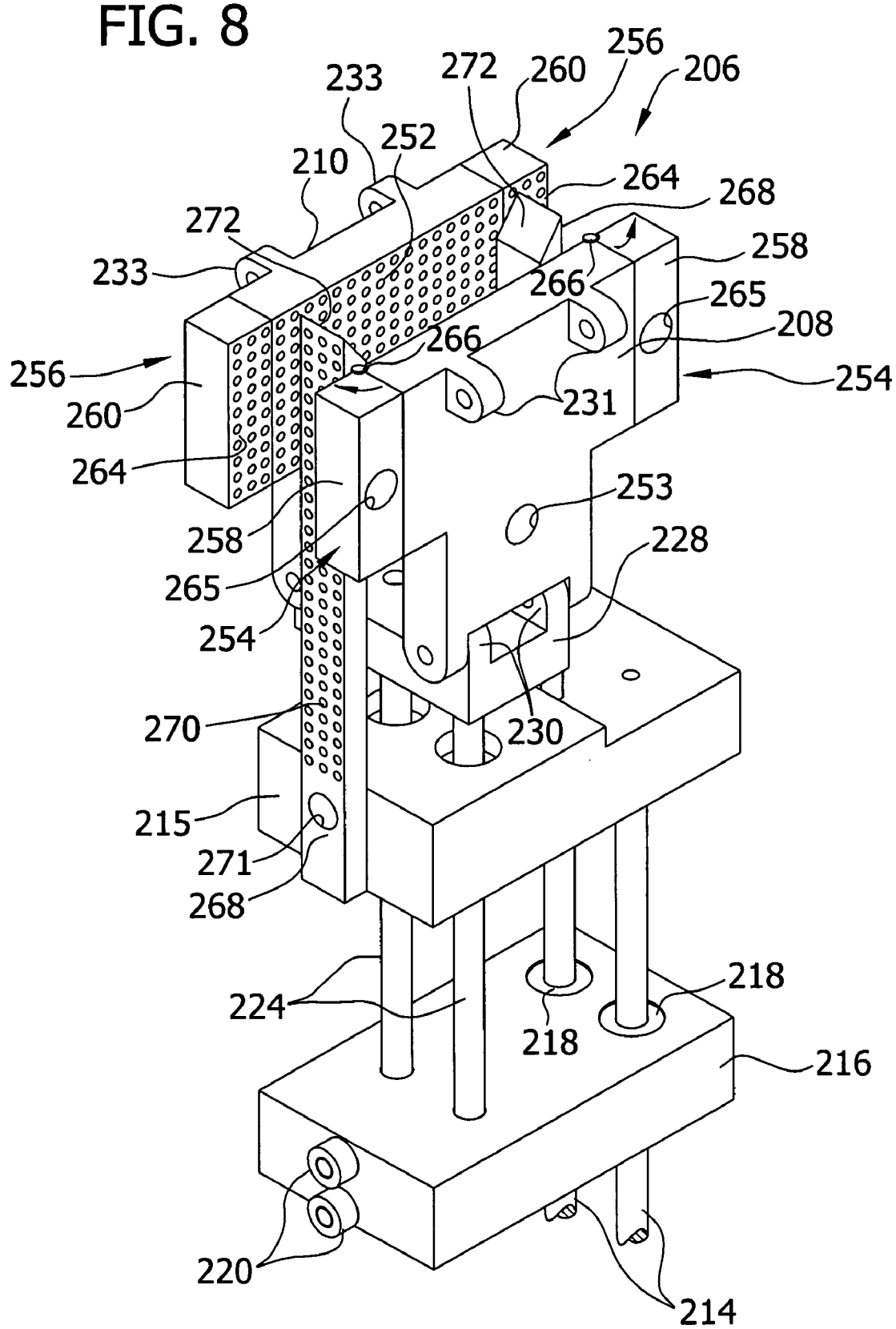
FIG. 8 is a fragmented perspective of a portion of the fastening apparatus of FIG. 6 including a longitudinal folding device, transverse folding devices and retention members.
Figure 9:
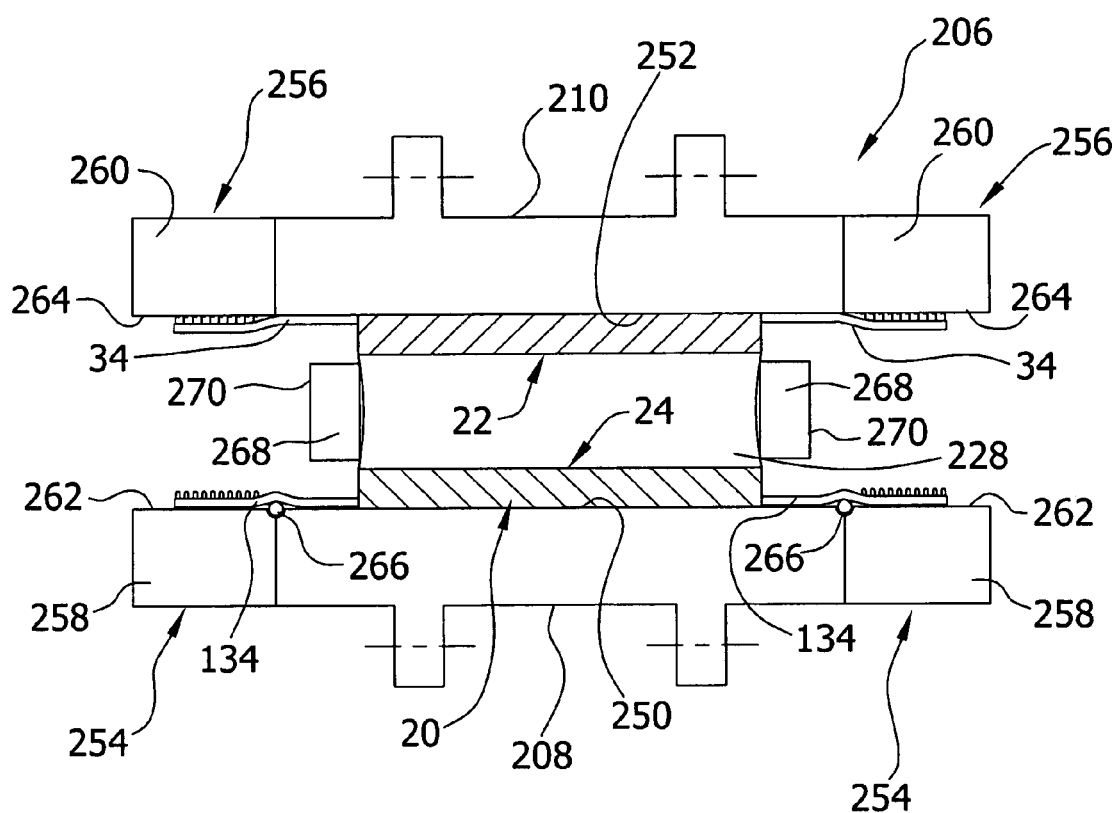
FIG. 9 is an end view of the longitudinal folding device, transverse folding devices and retention members of the fastening apparatus, with the longitudinal folding device in a folded configuration and an absorbent garment being folded by the folding device.

With reference to FIGS. 7 and 8, in the illustrated embodiment the longitudinal folding devices 206 are suitably mounted on the frame structure of the drum 202. In particular, for each folding device 206 a connecting member 212 is keyed to the central shaft 204 for rotation on the axis of the shaft. A pair of stationary rods 214 are each secured at one end (i.e., a radially inner end) to the connecting member 212 and extend radially outward therefrom. A stationary member 215 is mounted on the opposite (i.e., radially outer) ends of the stationary rods 214 and is connected to the frame structure 201 of the drum 202 (FIG. 6) to connect the drum to the driven central shaft 204. A slide member 216 is slidably mounted on the stationary rods 214 between the connecting member 212 and the stationary member 215 by suitable bearings 218 to permit sliding movement of the slide member relative to the drum 202. A pair of opposed cam followers 220 is secured to the slide member 216 and extend laterally outward from the slide member in spaced relationship with each other for receiving a cam track 222 therebetween. The cam track 222 extends 360 degrees around the central shaft 204 with the distance between the cam track and the shaft varying along the 360 degree path of the cam track in order to vary the radial position of the slide member 216 relative to the central shaft for reasons which will become apparent.

A pair of actuating rods 224 is secured at one end of each rod (i.e., their radially inner end) to the slide member 216 in parallel, spaced relationship with the stationary rods 214 for conjoint radial movement with the slide member. The actuating rods 224 are each received through the stationary member 215 and slidably mounted on the stationary member by suitable bearings 226. To the opposite ends (i.e., the radially outer end) of the actuating rods 224 a mounting member 228 is secured for conjoint radial movement with the slide member 216 and actuating rods 224 relative to the driven central shaft 204, stationary member 215 and drum 202. The mounting member 228 has two pair of pin mounts 230, each pair corresponding to a respective one of the longitudinal folding plates 208, 210 for pivotally mounting the folding plates on the mounting member.

Suitable links (not shown) are pivotally connected at one end to respective pin mounts 231 (FIG. 8) on the outer end of one of the folding plates 208 and pivotally connected at their opposite end to stationary structure such as the stationary member 215 or other frame structure 201 of the drum 202. Additional links (not shown) are pivotally connected at one end to respective pin mounts 233 on the outer end of the other folding plate 210 and pivotally connected at their opposite end to stationary structure such as the stationary member 215 or other frame structure 201 of the drum 202. Accordingly, it will be recognized that the folding plates 208, 210 and corresponding links between the pin mounts 231, 233 and stationary member 215 or other stationary frame structure 201 define a four bar linkage arrangement in which movement of the slide member 216 results in radial movement of the inner ends of the folding plates and the movement of the outer ends of the plates is defined by the four bar linkage arrangement.

Each of the longitudinal folding plates 208, 210 is configured to define an interior chamber (not shown) and a porous working surface 250 (FIGS. 9-12), 252 (i.e., the face on which the absorbent undergarment 20 is received onto the folding device as illustrated in FIG. 6)) to provide fluid communication between the interior chamber and ambient conditions exterior of the folding plates. The interior chamber of each longitudinal folding plate 208, 210 is in fluid communication with a suitable vacuum source (not shown), such as by one or more vacuum hoses (not shown) and suitable inlets 253 (FIG. 8) such that the longitudinal folding plates are each operable, and more suitably they are separately operable, in a vacuum mode in which vacuum pressure is applied to the interior chamber of the respective folding plate to thereby draw and retain the undergarment 20 against the porous working surface 250, 252 of the folding plate.

It is readily understood in the art that vacuum can be supplied by a vacuum shoe (not shown). While shown in the drawings, a vacuum shoe is a circular chamber supplied with vacuum that is either pressed against a wear plate or kept in close proximity (e.g., within 0.004 inches (0.1 mm) to minimize loss of vacuum. The vacuum shoe is stationary and has slugs (e.g., end caps) on its ends to turn on and off the vacuum. The wear plate is attached to the rotating member. As the wear plate rotates, holes or slots in its surface enter the vacuum shoe and receive vacuum or exit the vacuum shoe and have the vacuum turned off.

The longitudinal folding plates 208, 210 are each of a suitable length such that the working surface 250, 252 is at least as long as, and more suitably longer than, one-half the length of the discrete training pants 20 whereby upon receiving the training pants on the folding device (i.e., with the longitudinal axis of the training pants oriented longitudinally of the folding plates) one folding plate 210 (broadly, a first folding plate and otherwise referred to further herein as the front folding plate) draws against and retains thereon the front waist region 22 and more suitably the front half of the training pants and the other folding plate 208 (broadly, a second folding plate and otherwise referred to further herein as the back folding plate) draws against and retains thereon the back waist region 24 and more suitably the back half of the training pants. The front and back folding plates 210, 208 also each have a width suitable to extend laterally up to and more suitably laterally outward of the absorbent assembly 32 of the pants to be held on the folding plates. For example, the illustrated front and back folding plates 210, 208 extend laterally to within portions of the pants defined by the front and back side panels 34, 134, but laterally inward of the laterally outer portions of the side panels 34, 134 and more suitably laterally inward of the fastening portions of the side panels (e.g., of the fastening components 84, 82 in the illustrated embodiment). The fastening portions of the side panels 34, 134 thus suitably extend laterally outward of the front and back folding plates 210, 208.

Referring now to FIG. 8, a first pair of transverse folding devices, generally indicated at 256 are provided adjacent the front (i.e., first) folding plate 210 to facilitate handling of the front side panels 34, and more suitably the fastening portions of the front side panels, during movement of the undergarment 20 in the transport direction and a second pair of transverse folding devices, generally indicated at 254, is provided adjacent the back (i.e., second) folding plate 208 to facilitate handling of the back side panels 134, and more suitably the fastening portions of the back side panels, during movement of the undergarment in the transport direction. In the illustrated embodiment, the transverse folding devices 256 associated with the front folding plate 210 comprise a pair of laterally spaced, longitudinally extending side plates 260 positioned adjacent to, and more suitably secured to, the opposite lateral sides of the front folding plate. The transverse folding devices 254 associated with the back folding plate 208 comprise a pair of laterally spaced, longitudinally extending side plates 258 positioned adjacent to, and more suitably secured to, the opposite lateral sides of the back folding plate.

The length of each of the side plates 258, 260 is suitably longer than the respective side panels 134, 34 of the training pants 20, but may be less than the full length of the back and front folding plates 208, 210. Each side plate 258, 260 has a respective interior chamber (not shown) at least in part and more suitably entirely separate from the interior chamber of the respective back and front folding plate 208, 210. The width of each side plate 258, 260 is suitably sufficient to extend the side plate laterally out from the respective back and front folding plate 208, 210 up to and more suitably laterally beyond the corresponding back and front side panels 134, 34, more suitably laterally beyond the fastening portions of the side panels, and even more suitably beyond the lateral side edges of the training pants at the side panels of the training pants 20 to be pre-fastened.

Each side plate 258, 260 also has a porous working surface 262 (FIGS. 9-12), 264 to provide fluid communication between the interior chamber of the side plate and conditions exterior of the side plate. The interior chamber of each side plate 258, 260 is in fluid communication with a vacuum source (not shown), such as by a suitable vacuum hose (not shown) and respective inlets 265, for operating each of the side plates (i.e., the transverse folding devices) in a vacuum mode in which the respective front and back side panels 34, 134, or at least the fastening portions of the front and back side panels, are drawn against and retained on the porous working surfaces 262, 264 of the side plates. The vacuum source that communicates with the interior chambers of the side plates 258, 260 may be the same as the vacuum source that communicates with the interior chambers of the back and front folding plates 208, 210, or the vacuum source for the side plates may be separate from the vacuum source for the folding plates. Moreover, there may be one vacuum source that communicates with each of the side plates 258, 260, or one vacuum source for the side plates secured to the back folding plate 208 and another vacuum source for the side plates secured to the front folding plate 210, or one vacuum source for each of the side plates.

Figure 10:
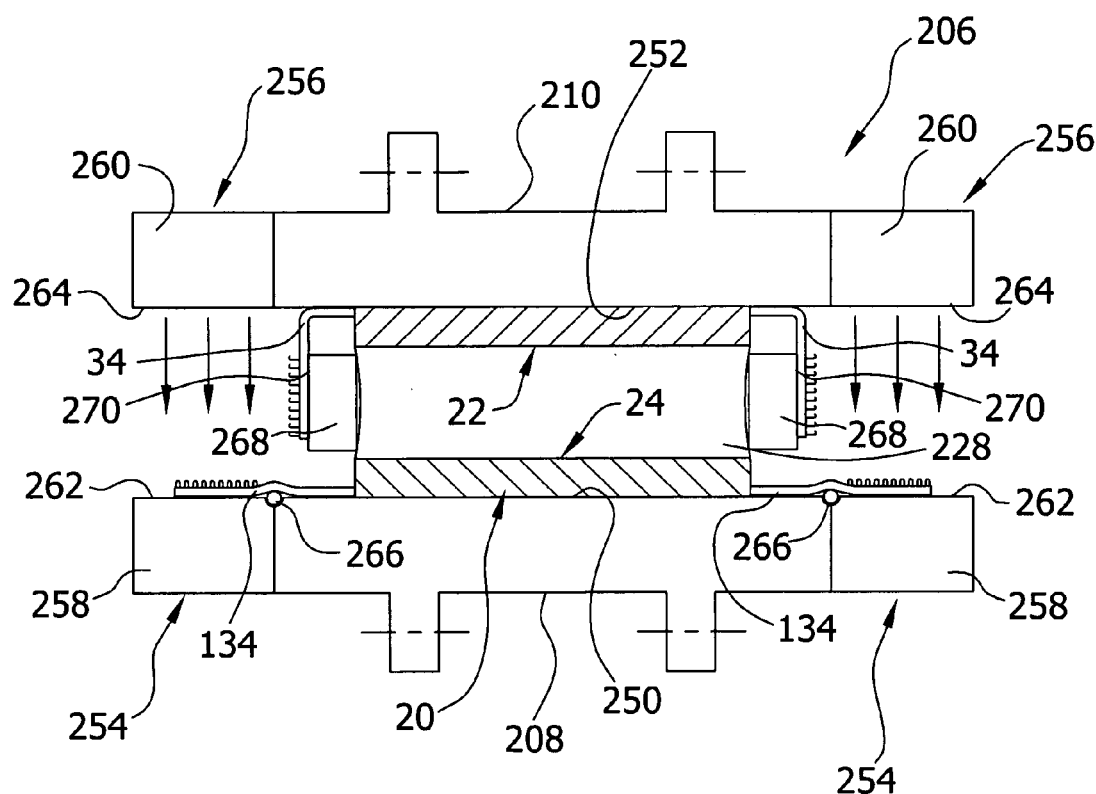
FIG. 10 is an end view similar to that of FIG. 9 with a pair of the transverse folding devices operating in a blowing mode to fold lateral fastening portions of the undergarment over the retention members.
Figure 11:
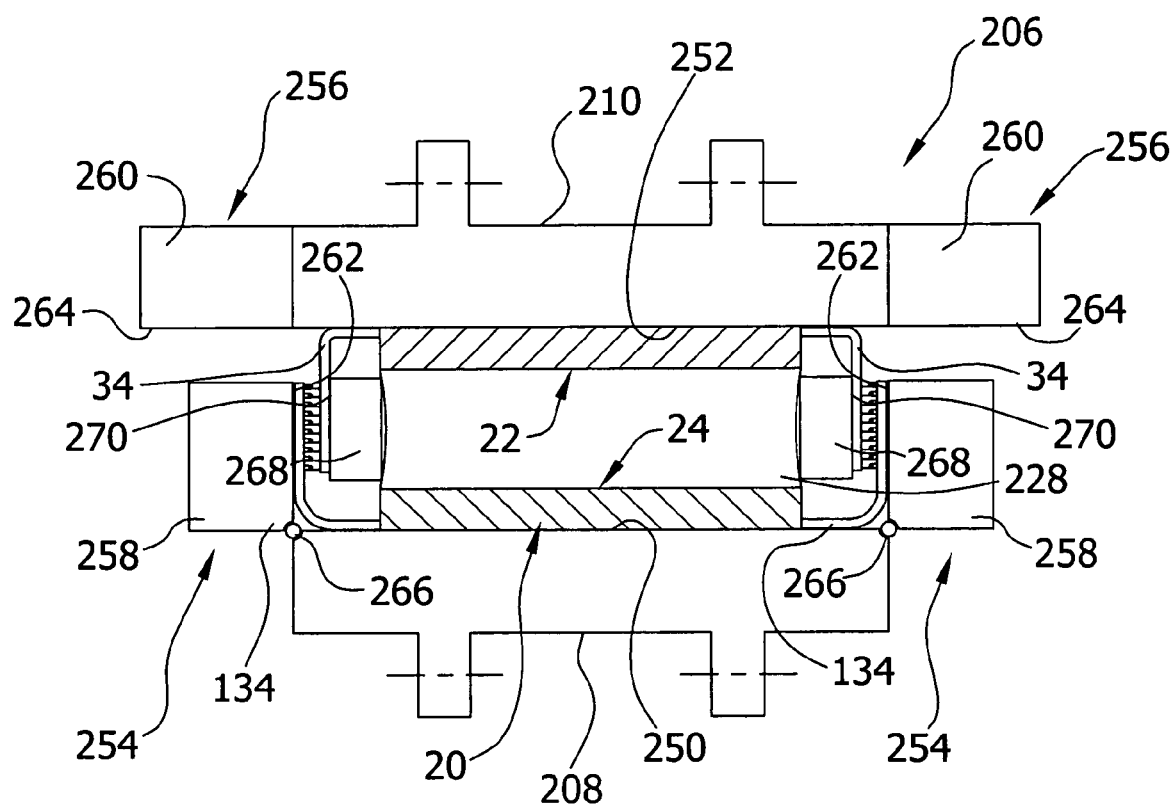
FIG. 11 is and end view similar to that of FIG. 9 with the opposite pair of transverse folding devices in a folded configuration to fold the opposite lateral fastening portions of the undergarment over the retention members.
Figure 12:
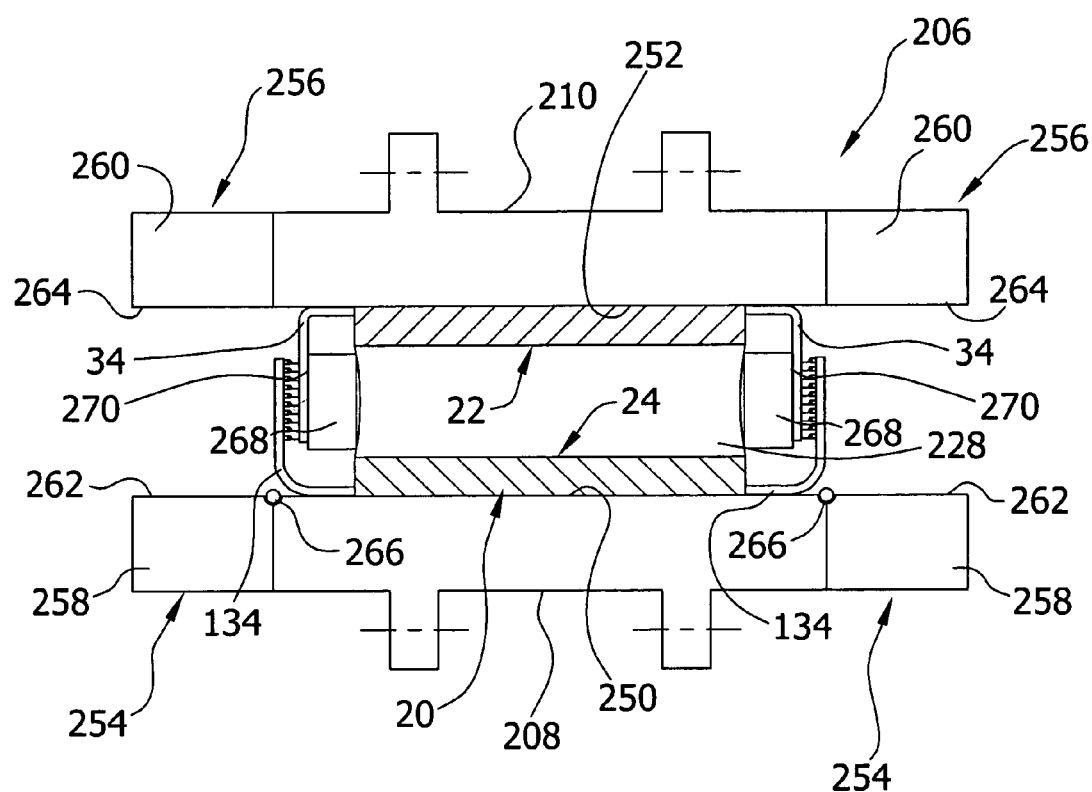
FIG. 12 is an end view similar to that of FIG. 9 with the undergarment in its pre-fastened configuration.

As illustrated best in FIG. 10, the side plates 260 (broadly, transverse folding devices 256) that are secured to the front folding plate 210 are suitably fixed against movement relative to the front folding plate. For example, in one embodiment these side plates 260 may be formed integrally with the front folding plate 210 and have a interior wall (not shown) separating the interior chambers of the side plates from the interior chamber of the front folding plate. In another embodiment these side plates may 260 be formed separate from the front folding plate 210 and secured thereto by any suitable securement technique such as welding, mechanical fastening and the like. The side plates 260 that are secured to the front folding plate 210 are each suitably operable between the vacuum mode described previously and a blowing mode in which pressurized gas (e.g., air) is delivered to the interior chamber of the side plate for flow outward through the porous working surface 264 of the side plate. For example, the vacuum source may be operable in reverse to deliver air to the interior chamber of the side plates 260, or the vacuum source may be shut down or otherwise shut off from fluid communication with the interior chambers of the side plates and a separate source (not shown) of pressurized gas is operated in fluid communication with the interior chambers of the side plates.

Each side plate 258 secured to the back folding plate 208 is suitably hinged thereto by a respective longitudinally extending hinge member 266 to permit hinged movement of the side plates (broadly, the transverse folding devices 254) relative to the back folding plate between an unfolded configuration (FIG. 10) in which the working surfaces 262 of the side plates are generally planar with the working surface 250 of the back folding plate, and a folded configuration (FIG. 11) in which the side plates are folded in toward the front folding plate 210, such as in the range of about 10 to about 100 degrees. In another embodiment, the side plates 258 secured to the back folding plate 208 may be fixed against movement relative thereto and be operable between the vacuum mode described previously and a blowing mode similar to the blowing mode described previously, and the side plates 260 secured to the front folding plate 210 may be hinged to the front folding plate for movement between an unfolded and folded configuration as described previously.

It is also understood that the side plates 258 secured to the back folding plate 208 and the side plates 260 secured to the front folding plate 210 may each be fixed against movement relative to the respective one of the back and front folding plates and be operable in both a vacuum mode and a blowing mode, or the side plates secured to the back folding plate may be hinged thereto and the side plates secured to the front folding plate may be hinged thereto without departing from the scope of this invention. It is further understood that the hinged side plates 258 may be capable of hinged movement and also be operable in both a vacuum mode and a blowing mode within the scope of the invention.

To facilitate proper alignment of and engagement between the fastening portions (e.g., fastening components 82, 84 in the illustrated embodiment) of the side panels 134, 34 of the undergarment 20, at least one retention member and more suitably a pair of laterally spaced retention members 268 are fixedly secured to stationary member 215 (or other frame structure of the drum 202) at each longitudinal folding device 206 for movement with the respective folding device in the transport direction. The retention members 268 are suitably transversely spaced from each other on opposite sides of the drum 202 generally at the transverse centerline between the back and front folding plates 208, 210 of each folding device 206 and extend radially relative to the drum. In particular, as seen best in FIG. 9, the retention members 268 are laterally located for interposition within the folding device 206, e.g., between the opposed back and front folding plates 208, 210 just laterally inward of the respective side plates 258, 260 in the closed configuration of the folding device 206 but spaced sufficiently to permit the crotch region 26 of the pants 20 to extend transversely between the retention members. Each retention member 268 has an interior chamber 269 (FIG. 7) and a laterally outward facing porous working surface to provide fluid communication between the interior chamber and conditions exterior of the retention member.

The interior chamber of each retention member 268 is in fluid communication with a vacuum source (not shown), such as by suitable vacuum hose (not shown) and respective inlets 271 (FIGS. 7 and 8), for operation of the retention member in a vacuum mode in which at least one of the front and back side panels 34, 134, and more suitably the fastener portion thereof is drawn against and retained on the retention member. As illustrated in FIGS. 6 and 7, the retention members 268 are sized in length and positioned relative to the back and front folding plates 208, 210 such that in the closed position of the folding device 206 (e.g., at angular position D in FIG. 6) the retention members each extend longitudinally (e.g., radially in the illustrated embodiment) a sufficient distance to be aligned with the side panels 34, 134 of the training pants 20. For example, the retention members 268 illustrated in FIG. 6 extend longitudinally slightly outward beyond the ends of the folding plates 208, 210 in the closed configuration of the folding device 206. In the open position of the folding device 206 (e.g., at angular position G in FIG. 6) a longitudinally outer or free end 272 of each of the retention members 268 is suitably approximately level with and more suitably longitudinally below (e.g., radially inward of) the working surfaces 250, 252 of the back and front folding plates 208, 210.

In operation according to one embodiment of a method for mechanically forming a pre-fastened absorbent undergarment, discrete partially assembled undergarments (e.g., training pants 20) are delivered sequentially from the source of partially assembled undergarments (e.g., from the assembly system 100, cutting roll 187 and vacuum anvil roll 188 in the illustrated embodiments of FIGS. 4 and 6) to the fastening apparatus 200 generally unfolded and unfastened. The drum 202 of the fastening apparatus 200 is continuously driven to rotate on the central shaft 204 so that the multiple longitudinal folding devices 206 on the drum sequentially pass by the vacuum anvil roll 188 to receive the training pants 20 onto the folding devices. At the angular position of the drum identified as angular position A in FIG. 6, the longitudinal folding plates 208, 210 of one longitudinal folding device 206 have just passed the vacuum anvil roll 188 with the folding device 206 in its open configuration, i.e., with the folding plates spread apart and in generally planar relationship with each other tangential to the drum 202, and the side plates 258 (broadly, the transverse folding devices 254) secured to the back folding plate 208 in their unfolded position planar with the back folding plate.

A discrete, partially assembled pair of training pants 20 has been received by the longitudinal folding plates 208, 210 and the folding plates and corresponding side plates 258, 260 are each operated in their respective vacuum mode to draw and retain the training pants 20 on the folding plates and side plates, with the front waist region 22 and more suitably the front one-half of the training pants 20 being drawn against and retained on the working surface 252 of the front folding plate 210, the front side panels 34 and more suitably the fastening portions of the front side panels drawn against and retained on the working surfaces 264 of the laterally opposite side plates 260 secured to the front folding plate. The back waist region 24 and more suitably the back one-half of the training pants are drawn against and retained on the working surface 250 of the back folding plate 208 and the back side panels 134 and more suitably the fastening portions of the back side panels drawn against and retained on the working surfaces 262 of the laterally opposite side plates 258 secured to the back folding plate.

As the drum 202 further carries the training pants 20 in the transport direction (e.g., the counter-clockwise direction in the illustrated embodiment) to the angular position indicated in FIG. 6 as position B, the cam followers 220 follow the varying cam track 222 to pull the slide member 216, actuating rods 224 and folding device 206 radially inward relative to the drum. This motion results in radially inward movement of the inner ends of the back and front folding plates 208, 210 to initiate folding of the longitudinal folding plates (and the side plates 258, 260 that are secured thereto), and hence the training pants 20 retained thereon, relative to the drum 202 toward the closed configuration of the longitudinal folding device. While not illustrated in the drawings, it is contemplated that a transverse tucking blade (e.g., a rotating or reciprocating tucking blade) separate from the folding device may contact and push against the crotch region 26 of the pants as folding of the pants is initiated to facilitate creasing of the pants as the pants are folded. However, it is understood that the tucking blade may be omitted without departing from the scope of this invention.

At angular position C of the drum 202, the folding plates 208, 210 are folded further inward toward the closed configuration of the longitudinal folding device 206. Upon further rotation of the drum 202 to angular position D, the back and front folding plates 208, 210 (and hence the corresponding side plates 258, 260 respectively secured thereto) are in opposed relationship with each other in the closed configuration of the folding device 206. Accordingly, the training pants 20 are folded so that the front and back waist regions (i.e., the first and second end regions) 22, 24 of the pants are in opposed relationship with each other, as are the front and back side panels 34, 134 of the training pants.

The side plates 260 (broadly, the first transverse folding devices 256) that are secured to the front folding plate 210 are then operated in their blowing mode (i.e., instead of the vacuum mode) to deliver a flow of pressurized gas outward through the porous working surfaces 264 of the side plates. The pressurized gas urges the front side panels 34, and more suitably the fastening portions (i.e., first fastening portions) thereof, to fold inward toward back side panels 134, and more suitably the fastening portions (i.e., second fastening portions) thereof, and over the working surfaces 270 of the retention members 268 which are operating in their vacuum mode to draw the front side panels (and more particularly the fastening portions of the front side panels) against the working surfaces of the retention members as illustrated in FIG. 10 for retention thereon. In this manner, the fastening portions (e.g., the fastening components 84 or hook fasteners in the illustrated embodiments) on the front side panels 34 face outward away from the working surfaces 270 of the retention members 268. Upon rotation of the drum 202 to angular position E in the embodiment of FIG. 6, the hinged side plates 258 (broadly, the second transverse folding devices 254) secured to the back folding plate 208 are rotated in toward their folded position to thereby fold the back side panels 134 and more suitably the fastening portions (i.e., second fastening portions) of the back side panels, over the working surfaces 270 of the retention members 268 and more particularly over the folded front side panels 34 (and more suitably the fastening portions, i.e., first fastening portions, of the front side panels) retained by the retention member. Accordingly, the fastening components 82 (e.g., the loop fasteners) on the front side panels 134 fastenably engage the fastening components 84 on the back side panels 34 to secure the front and back side panels together.

Operation of the hinged side plates 258 in the vacuum mode is then stopped to permit separation of the hinged side plates from the back side panels 134 (and more particularly the fastening portions of the back side panels) upon rotation of the side plates back to their initial unfolded position planar with the back folding plate 208, leaving the front and back side panels 34, 134 engaged together and retained on the retention members 268. It is understood that the vacuum provided by the retention members 268 may be sufficient to draw both of the overlapped and engaged front and back side panels 34, 134 against the retention members, or it may be sufficient only to draw the underlying one (e.g., the back side panels in the illustrated embodiment) of the side panels against the retention members with the overlapping side panels being held by fastenable engagement with the underlying side panel.

Operation of the retention members 268 in their vacuum mode is subsequently stopped (e.g., by shutting down the vacuum source or otherwise closing off fluid communication between the vacuum source and the interior chambers 269 of the retention members), as the drum 202 rotates further towards angular position F. Vacuum to the front folding plate 210 is also decreased, and more suitably stopped, as the drum 202 rotates toward angular position F. The cam followers 220 follow the cam track 222 to move the sliding member 216, actuating rods 224 and hence the folding device 206 radially outward, thereby unfolding the back and front folding plates 208, 210 toward the open configuration of the folding device. The folded and now pre-fastened training pants 20 are still drawn against and retained on the working surface 250 of the back folding plate 208 as the folding device 206 is moved toward its open configuration as illustrated at angular position F of FIG. 6. The fastened side panels 34, 134 ride up (e.g., radially outward) along the working surfaces 270 of the retention members 268 until the side panels are clear of the free ends 272 of the retention members (i.e., the retention members are no longer within the interior space 53 of the pre-fastened training pants 20). At angular position G of the drum 202, the folding device 206 is in its fully open configuration, with the folded and pre-fastened training pants 20 laying generally flat against and being held on the working surface 250 of the back folding plate 208.

The drum 202 rotates further to angular position H at which the folding plates 258, 260, in the open configuration of the folding device 206, are in generally opposed relationship with a suitable transfer device, such as the conventional vacuum box conveyor 274 illustrated in FIG. 6. The vacuum box conveyor 274 draws the pre-fastened training pants 20 off of the folding device 206 and transfers the training pants downstream of the folding device for further processing. In one embodiment, the vacuum pressure of the vacuum box conveyor 274 is suitably greater than that holding the training pants 20 on the front folding plate 208 so as to draw the training pants away from the front folding plate. Alternatively, or additionally, it is understood that the vacuum to the interior chamber of the front folding plate may be decreased or even terminated to further facilitate the transfer of the training pants 20 to the transfer device 274. In another embodiment, the transfer device 274 may comprise a simple (e.g., non-vacuum) conveyor or other transfer device and the training pants 20 may be transferred onto the conveyor by gravity, or by operating the back folding plate 208 in a blowing mode to blow pressurized gas out through the working surface 250 of the back folding plate, thereby urging the training pants away from the folding plate and onto the conveyor, or by other suitable techniques.

The folding plates 208, 210 suitably remain in the open configuration of the folding device 206 as the drum 202 rotates through angular positions I and J until the drum has completed a full 360 degree rotation and returns to angular position A.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for mechanically forming a pre-fastened absorbent undergarment during initial manufacture of said undergarment, said absorbent undergarment having a longitudinal axis, a lateral axis, a first longitudinal end region, a second longitudinal end region and a central region longitudinally intermediate and interconnecting the first and second end regions, a first fastening portion at said first end region and a second fastening portion at said second end region spaced longitudinally from and engageable with the corresponding first fastening portion to secure the absorbent undergarment in its pre-fastened configuration, said method comprising:

partially assembling the absorbent undergarment to have a configuration in which the undergarment is generally unfolded and the first and second fastening portions are unfastened;

transporting the absorbent undergarment in a transport direction;

folding the absorbent undergarment longitudinally such that the first and second end regions of the undergarment are in generally opposed relationship with each other, said longitudinal folding step being performed while transporting said partially assembled garment in the transport direction;

urging the first fastening portion to fold in toward the second fastening portion and toward the working surface of a retention member, this first urging step being performed while transporting said undergarment and said retention member in the transport direction;

operating the retention member to draw against and retain thereon the first fastening portion, said operating step being performed while transporting said undergarment and said retention member in the transport direction; and urging the second fastening portion to fold in toward the said first fastening portion retained on the working surface of the retention member for overlapping relationship between said first and second fastening portions to thereby facilitate fastening engagement therebetween while retaining said first fastening portion on the working surface of the retention member, this second urging step being performed while transporting the undergarment and the retention member in the transport direction.

2. The method set forth in claim 1 wherein the transport direction in which the garment is transported is arcuate.

3. The method set forth in claim 1 wherein the step of operating the retention member comprises operating the retention member to draw a vacuum on the first fastening portion of the undergarment.

4. The method set forth in claim 1 wherein the first urging step comprises directing pressurized gas to flow against said first fastening portion to urge said first fastening portion to fold in toward the second fastening portion and over the working surface of the retention member.

5. The method set forth in claim 1 wherein the second urging step comprises retaining the second fastening portion against a transverse folding device while moving the transverse folding device relative to the retention member into generally opposed relationship with the working surface of the retention member to thereby fold the second fastening portion over the first fastening portion and into engagement therewith.

6. The method set forth in claim 5 wherein the undergarment has an inner surface and an outer surface, the first urging step comprising urging the inner surface of the undergarment at said first fastening portion to fold in toward the second fastening portion and toward the working surface of the retention member such that the inner surface of the undergarment at said first fastening portion is drawn against and retained on the working surface of the retention member, the outer surface of the undergarment at said first fastening portion facing away from the working surface of the retention member, the second urging step comprising retaining the outer surface of the second fastening portion against the transverse folding device while moving the transverse folding device relative to the retention member to thereby fold the second fastening portion over the first fastening portion such that the inner surface of second fastening portion is opposed with and engages the outer surface of the first fastening portion retained on the retention member.

7. The method set forth in claim 1 wherein the undergarment has an inner surface and an outer surface, the folding step comprising retaining the outer surface of the undergarment at substantially the entire first and second end regions of the undergarment including the entire first and second fastening portions thereof on a folding device in a generally unfolded configuration of the folding device and operating the folding device to move the folding device to a folded configuration in which the first and second end regions of the undergarment are in generally opposed relationship with each other.

8. A method for mechanically forming a pre-fastened absorbent undergarment during initial manufacture of said undergarment, said absorbent undergarment having a longitudinal axis, a lateral axis, a first longitudinal end region, a second longitudinal end region and a central region longitudinally intermediate and interconnecting the first and second end regions, a first fastening portion at said first end region and a second fastening portion at said second end region spaced longitudinally from and engageable with the corresponding first fastening portion to secure the absorbent undergarment in its pre-fastened configuration, said method comprising:

partially assembling the absorbent undergarment to have a configuration in which the undergarment is generally unfolded and the first and second fastening portions are unfastened;

transporting the absorbent undergarment in a transport direction;

folding the absorbent undergarment longitudinally such that the first and second end regions of the undergarment are in generally opposed relationship with each other, said longitudinal folding step being performed while transporting said partially assembled garment in the transport direction;

folding the first fastening portion in toward the second fastening portion while transporting said undergarment in the transport direction; and retaining substantially the entire second fastening portion on a transverse folding device while moving the transverse folding device relative to the first fastening portion to a position in which the transverse folding device is in generally opposed relationship with the first fastening portion with the second fastening portion retained on the transverse folding device and disposed between the transverse folding device and the first fastening portion such that the second fastening portion fastenably engages the first fastening portion.

9. The method set forth in claim 8 wherein the undergarment has an inner surface and an outer surface, the folding step comprising retaining the outer surface of the undergarment at substantially the entire first and second end regions of the undergarment including the entire first and second fastening portions thereof on a folding device in a generally unfolded configuration of the folding device and operating the folding device to move the folding device to a folded configuration in which the first and second end regions of the undergarment are in generally opposed relationship with each other.

* * * * *